United States Patent
Qu et al.

(10) Patent No.: US 8,735,585 B2
(45) Date of Patent: May 27, 2014

(54) INDENOPYRIDINE DERIVATIVES

(75) Inventors: Bo Qu, Brookfield, CT (US); Anjan Saha, Hamden, CT (US); Jolaine Savoie, Danbury, CT (US); Xudong Wei, Ridgefield, CT (US); Nathan K. Yee, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/584,872

(22) Filed: Aug. 14, 2012

(65) Prior Publication Data

US 2013/0211089 A1 Aug. 15, 2013

Related U.S. Application Data

(60) Provisional application No. 61/524,551, filed on Aug. 17, 2011.

(51) Int. Cl.
*C07D 221/16* (2006.01)
*C07D 211/20* (2006.01)
*C07D 255/00* (2006.01)
*A61K 31/44* (2006.01)

(52) U.S. Cl.
USPC ........... 546/111; 546/347; 558/425; 514/290; 514/358

(58) Field of Classification Search
USPC .......................................... 514/290; 546/111
See application file for complete search history.

(56) References Cited

U.S. PATENT DOCUMENTS

| | | | |
|---|---|---|---|
| 3,341,538 A | 9/1967 | Block et al. | |
| 3,378,587 A | 4/1968 | Reinhardt | |
| 3,474,106 A | 10/1969 | Ziering et al. | |
| 3,703,529 A | 11/1972 | Cavalla et al. | |
| 3,823,150 A | 7/1974 | Merz et al. | |
| 3,856,795 A | 12/1974 | Yardley | |
| 3,919,047 A | 11/1975 | Vidic et al. | |
| 3,931,194 A | 1/1976 | Merz et al. | |
| 3,981,874 A | 9/1976 | Merz et al. | |
| 4,009,171 A | 2/1977 | Albertson | |
| 4,043,927 A | 8/1977 | Duling et al. | |
| 4,108,857 A | 8/1978 | Albertson | |
| 4,166,174 A | 8/1979 | Tanaka et al. | |
| 4,268,673 A | 5/1981 | Akkerman et al. | |
| 5,354,758 A | 10/1994 | Lawson et al. | |
| 5,607,941 A | 3/1997 | Merz et al. | |
| 6,145,103 A | 11/2000 | Typaldos et al. | |
| 6,368,816 B2 | 4/2002 | Walker et al. | |
| 6,838,253 B2 | 1/2005 | Walker et al. | |
| 6,946,487 B2 | 9/2005 | Walker et al. | |
| 7,087,400 B2 | 8/2006 | Walker et al. | |
| 7,122,531 B2 | 10/2006 | Walker et al. | |
| 7,122,532 B2 | 10/2006 | Walker et al. | |
| 7,129,231 B2 | 10/2006 | Walker et al. | |
| 7,897,773 B2 | 3/2011 | Aletru et al. | |
| 8,048,825 B2 | 11/2011 | Hino et al. | |
| 2006/0089349 A1 | 4/2006 | Gundertofte et al. | |
| 2006/0194780 A1 | 8/2006 | Nargund et al. | |
| 2009/0170894 A1 | 7/2009 | Aletru et al. | |
| 2010/0256363 A1 | 10/2010 | Xu | |
| 2011/0015157 A1 | 1/2011 | Claremon et al. | |
| 2011/0028445 A1 | 2/2011 | Eckhardt et al. | |
| 2011/0112062 A1 | 5/2011 | Claremon et al. | |
| 2011/0136800 A1 | 6/2011 | Eckhardt et al. | |
| 2011/0190262 A1 | 8/2011 | Himmelsbach et al. | |
| 2011/0263583 A1 | 10/2011 | Claremon et al. | |
| 2011/0269736 A1 | 11/2011 | Eckhardt et al. | |
| 2011/0269791 A1 | 11/2011 | Peters et al. | |
| 2011/0275595 A1 | 11/2011 | Eckhardt et al. | |
| 2012/0108579 A1 | 5/2012 | Renz et al. | |
| 2012/0115853 A1 | 5/2012 | Eckhardt et al. | |
| 2012/0172357 A1 | 7/2012 | Himmelsbach | |

FOREIGN PATENT DOCUMENTS

| | | |
|---|---|---|
| CA | 1049008 A1 | 2/1979 |
| CA | 1049511 A1 | 2/1979 |
| CA | 1056377 A1 | 6/1979 |
| CA | 1107280 A1 | 8/1981 |
| DE | 2105743 A1 | 8/1972 |
| DE | 2108954 A1 | 9/1972 |
| DE | 2229695 A1 | 1/1974 |
| DE | 2338369 A1 | 2/1975 |
| DE | 2354002 A1 | 5/1975 |
| DE | 2411382 A1 | 9/1975 |
| DE | 2437610 A1 | 2/1976 |
| DE | 2828039 A1 | 1/1980 |

(Continued)

OTHER PUBLICATIONS

Abstract in English for JP2007140188 publication date 2007.
Caplus-133:4656—Anantanarayan, A. et. al., "Preparation of heteroarylpyrazoles as P38 kinase inhibitors". 2000.
Caplus-147:134403, Hembrough, T.A., et al., Composition and methods comprising proteinase activated receptor 2 antagonists for treatment of angiogenesis and inflammatory disorders and cancer. 2007.
Caplus-77:5360, Helsley, G. C. "Antispasmodic 8-carbamoyl-3-phenylnortropanes". 1972.
ChemAbstract-Accession No. 958599-31-0, Chemical Abstracts Service, Columbus, Ohio, Source: Emory MLSC database, Dec. 2007.
ChemAbstract-Accession No. 958625-83-7, Chemical Abstracts Service, Columbus, Ohio, Source: Emory MLSC database, Dec. 2007.
ChemAbstract-Accession No. 958629-14-6, Chemical Abstracts Service, Columbus, Ohio, Source: Emory MLSC database, Dec. 2007.

(Continued)

*Primary Examiner* — Janet L Andres
*Assistant Examiner* — Daniel Carcanague
(74) *Attorney, Agent, or Firm* — Michael P. Morris; David L. Kershner

(57) ABSTRACT

Disclosed is a compound of formula (I)

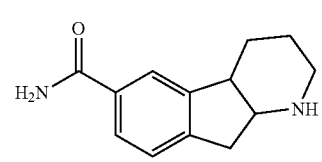

(I)

and salts thereof. Also disclosed are methods of making the compound of formula (I) and the use of the compound as an intermediate for making pharmaceutically active compounds such as 11-β-hydroxysteroid hydrogenase type 1 (11-β-HSD1) inhibitors.

9 Claims, No Drawings

(56) References Cited

FOREIGN PATENT DOCUMENTS

| | | |
|---|---|---|
| DE | 10034623 A1 | 1/2002 |
| EP | 0847275 A1 | 6/1998 |
| EP | 1864971 A1 | 12/2007 |
| EP | 1935420 A1 | 6/2008 |
| FR | 2796940 A1 | 2/2001 |
| GB | 1077711 A | 8/1967 |
| JP | 2003057815 A | 2/2003 |
| JP | 2006342093 A | 12/2006 |
| JP | 2007015930 A | 1/2007 |
| JP | 2007016223 A | 1/2007 |
| JP | 2007140188 A | 6/2007 |
| JP | 2007269721 A | 10/2007 |
| JP | 2011519374 A | 7/2011 |
| WO | 1994013641 A1 | 6/1994 |
| WO | 9637494 A1 | 11/1996 |
| WO | 9707789 A1 | 3/1997 |
| WO | 9822462 A1 | 5/1998 |
| WO | 9852940 A1 | 11/1998 |
| WO | 0155063 A1 | 8/2001 |
| WO | 03097608 A2 | 11/2003 |
| WO | 2004089896 A1 | 10/2004 |
| WO | 2005108360 A1 | 11/2005 |
| WO | 2005108361 A1 | 11/2005 |
| WO | 2006024628 A1 | 3/2006 |
| WO | 2006040329 A1 | 4/2006 |
| WO | 2006044174 A2 | 4/2006 |
| WO | 2007051810 A2 | 5/2007 |
| WO | 2007076055 A2 | 7/2007 |
| WO | 2007081570 A2 | 7/2007 |
| WO | 2007124337 A1 | 11/2007 |
| WO | 2007127693 A1 | 11/2007 |
| WO | 2007127763 A2 | 11/2007 |
| WO | 2008000951 A2 | 1/2008 |
| WO | 2008059948 A1 | 5/2008 |
| WO | 2008106128 A2 | 9/2008 |
| WO | 2009017664 A1 | 2/2009 |
| WO | 2009017671 A1 | 2/2009 |
| WO | 2009061498 A1 | 5/2009 |
| WO | 2009063061 A2 | 5/2009 |
| WO | 2009100872 A1 | 8/2009 |
| WO | 2009102428 A2 | 8/2009 |
| WO | 2009102460 A2 | 8/2009 |
| WO | 2009117109 A1 | 9/2009 |
| WO | 2009134400 A1 | 11/2009 |
| WO | 2009138386 A2 | 11/2009 |
| WO | 2010010157 A2 | 1/2010 |
| WO | 2010010174 A1 | 1/2010 |
| WO | 2010011314 A1 | 1/2010 |
| WO | 2010023161 A1 | 3/2010 |
| WO | 2010046445 A2 | 4/2010 |
| WO | 2010139673 A1 | 12/2010 |
| WO | 2011057054 A1 | 5/2011 |
| WO | 2012061708 A1 | 5/2012 |

OTHER PUBLICATIONS

ChemAbstract-Accession No. 958629-22-6, Chemical Abstracts Service, Columbus, Ohio, Source: Emory MLSC database, Dec. 2007.
ChemAbstract-Accession No. 958629-39-5, Chemical Abstracts Service, Columbus, Ohio, Source: Emory MLSC database, Dec. 2007.
ChemAbstract-Accession No. 958696-32-7, Chemical Abstracts Service, Columbus, Ohio, Source: Emory MLSC database, Dec. 2007.
ChemAbstract-Accession No. 958696-39-4, Chemical Abstracts Service, Columbus, Ohio, Source: Emory MLSC database, Dec. 2007.
ChemAbstract-Accession No. 958700-63-5, Chemical Abstracts Service, Columbus, Ohio, Source: Emory MLSC database, Dec. 2007.
Hughes, K.A. et al., "11-beta-hydroxysteroid dehydrogenase type 1 (11b-HSD1) inhibitors in Type 2 diabetes mellitus and obesity". Expert Opinion, Investig. Drugs, 17(4), 2008, pp. 481-496.
WO09017664 Published Feb. 5, 2009. Applicant: Vitae Pharmaceuticals, Inc. Inventor: D. A. Claremon et al.
De Luis et al., Control of Metabolic Syndrome with Metformin in Obese Type 2 Diabetes Mellitus Patients, Diabetes Research and Clinical Practice, 2000, vol. 50, Suppl. 1, pp. S51-S52.
Gutkowska, et al, Acta Poloniae Pharmaceutica, 1982, 39, p.61-64.
Olesen, Preben H.; the Use of Bioisosteric Groups in Lead Optimization; Current Opinion in Drug Discovery & Development (2001) vol. 4, No. 4 pp. 471-478.
Patani, George A. et al., "Bioisosterism: A Rational Approach in Drug Design" Chem. Rev. (1996) vol. 96, pp. 3147-3176.
Thornber, C.W.; Isosterism and Molecular Modification in Drug Design; Chem. Soc, Rev (1979) vol. 8 pp. 563-580.
Abstract in English for German DE10034623, publication date Jan. 31, 2002.
Abstract in English for German DE2105743, publication date Aug. 31, 1972.
Abstract in English for German DE2108954, publication date Sep. 7, 1972.
Abstract in English for JP2003057815, publication date Feb. 28, 2003.
Abstract in English for JP2006342093, publication date Dec. 21, 2006.
Abstract in English for JP2007016223, publication date Jan. 25, 2007.
Abstract in English for JP2007269721, publication date Oct. 18, 2007.
Bosch, J. et al., "Benzomorphan Related Compounds. A Versatile Method For The Synthesis of Heteromorphans." Heterocycles, 1980, vol. 14, No. 12, pp. 1983-1988.
Demarinis, R. M. et al., "a-Adrenergic Agents, 1. Direct-Acting a1 Agonists Related to Methoxamine." Journal of Medicinal Chemistry, 1981, vol. 24, No. 12, pp. 1432-1437.
Eberle, M. K. et al., "Carbocyclic Phenylhydrazines In The Fischer Indole Synthesis-II." Tetrahedron, 1973, vol. 29, No. 24, pp. 4049-4052.
Harno, E. et al., "Will treating diabetes with 11b-HSD1 inhibitors affect the HPA axis?" Trends in Endocrinology and Metabolism, 2010, vol. 21, No. 10, pp. 619-627.
International Search Report and Written Opinion for PCT/US2012/050679 mailed Oct. 31, 2012.
Kametani, T. et al., "Azabenzomorphane and Related Compounds." Chem. Pharma. Bull., 1965, vol. 13, No. 3, pp. 295-299.
Ma, Z. et al., "A Concise Formal Synthesis of Unnatural (+)-Aphanorphine from (2S,4R)-4-Hydroxyproline." Synlett, 2007, No. 1, pp. 161-163.
Ma, Z. et al., "Formal Syntheses of (-)- and (+)-aphanorphine from (25,4R)-4-hydroxyproline." Tetrahedron, 2007, 63, pp. 7523-7531.
Masamune, T. et al., "The Synthesis and the Exhaustive Methylation of the cis and trans Isomers of 1,2,3,4,4a,5,6,10b-Octahydrophenanthridine and 1,2,3,4,4a,5,6,10b-Octahydrobenzo[f]quinoline." Journal of Organic Chemistry, 1964, vol. 29, No. 6, pp. 1419-1424.
Mehta, P. et al., "Synthesis of cis & trans-1-substituted 1,2,3,4,4a,5,11,11a-octahydro-6H-pyrido[3,2-b]carbazoles, 4- substituted 1,2,3,4,4a,5,6,11c-octa-hydro-7H-pyrido[2,3,-c]carbazoles, cis-4-methy1-1,2,3,4,4a,5,6,12b-octa-hydro-7H-pyrido[2,3-c]acridine & cis-1-methy1-1,2,3,4,4a,5,12,12a-octa-hydro-6H-pyrido[3,2-13]-acridine-A new class of potential antiparkinsonian agents." Indian Journal of Chemistry, 1991, vol. 30B, No. 2, pp. 213-221.
Rosenstock, J. "The 11-b-Hydroxysteroid Dehydrogenase Type 1 Inhibitor INCB13739 Improves Hyperglycemia in Patients With Type 2 Diabetes Inadequately Contolled by Metformin Monotherapy." Diabetes Care, 2010, vol. 33, No. 7, pp. 1516-1522.
Serajuddin, Abu T.M., "Salt formation to improve drug solubility." Advanced Drug Delivery Reviews 59, 2007, pp. 603-616.
Stewart, P. et al., "11b-Hydroxysteroid Dehydrogenase." Advances in Research and Applications, 1999, vol. 57, pp. 249-324.
Tadayyon, M. et al., "Insulin sensitisation in the treatment of Type 2 diabetes." Expert Opinion on Investigational Drugs, 2003, vol. 12, No. 3, pp. 307-324.
Yokoyama, N. et al., "Syntheses, Analgetic Activity, and Physical Dependence Capacity of 5-Phenyl-6,7- benzomorphan Derivatives." Journal of Medicinal Chemistry, 1979, vol. 22, No. 5, pp. 537-553.

INDENOPYRIDINE DERIVATIVES

TECHNICAL FIELD

This application relates to indenopyridine derivatives. The indenopyridine derivatives of the invention are useful as intermediates for the preparation of pharmaceutically active compounds such as 11-β-hydroxysteroid hydrogenase type 1 (11-β-HSD1) inhibitors.

BACKGROUND OF THE INVENTION

Aryl- and heteroarylcarbonyl derivatives of hexahydroindenopyridines are reportedly useful as inhibitors of 11-β-hydroxysteroid hydrogenase type 1 ("11-β-HSD1") and for treatment of disorders associated with 11β-HSD1 activity including, for example, diabetes mellitus (e.g., type II diabetes), obesity, symptoms of metabolic syndrome, glucose intolerance, hyperglycemica (see, e.g., WO 2011/057054).

The aryl- and heteroarylcarbonyl derivatives of hexahydroindenopyridines can be prepared, for example, from nitrile-substituted hexahydroindenopyridines as described in WO 2011/057054. In one method described in WO 2011/057054, the intermediate (4aR,9aS)-2,3,4,4a,9,9a-hexahydro-1H-indeno[2,1-b]pyridine-6-carbonitrile (A) is allowed to react with 1H-benzoimidazole-5-carboxylic acid (B) followed by reaction with hydrogen chloride to provide the 11-β-HSD1 inhibitor (4a-R,9a-S)-1-(1H-benzoimidazole-5-carbonyl)-2,3,4,4a,9,9a-hexahydro-1H-indeno[2,1-b]pyridine-6-carbonitrile (C) as depicted below:

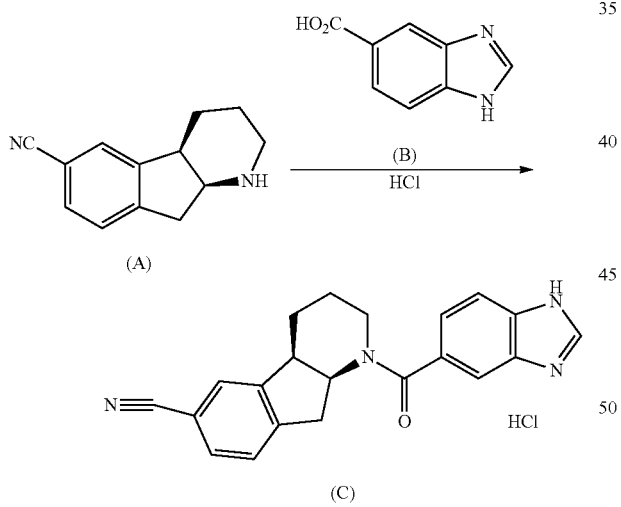

Methods of preparing the compound of formula (A) described in WO 2011/057054 include a 13-step synthesis and a low overall yield (~2.9%). In addition, some of the described methods utilize corrosive and/or toxic reagents (e.g., trifluoromethanesulfonic acid anhydride (Tf$_2$O), boron tribromide (BBr$_3$) and Zinc cyanide (Zn(CN)$_2$), which produce a problematic by-product stream. Thus, there is a need, for improved processes for making compounds of formula (A). Such improvements in making intermediate (A) will allow for more efficient preparation of aryl- and heteroarylcarbonyl derivatives of hexahydroindenopyridines inhibitors, particularly for large-scale production.

BRIEF SUMMARY OF THE INVENTION

The invention relates to indenopyridine derivatives and salts thereof. In one embodiment, the invention relates to a compound of formula (I):

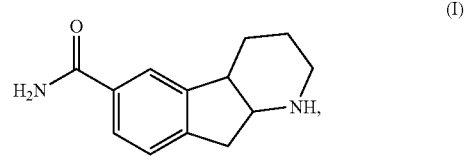 [SMILES: NC(=O)c1ccc2c(c1)C1CCCNC1C2]

or a salt thereof.

In another embodiment, the invention relates to a compound of formula (I) in free-base form.

In another embodiment, the invention relates to a salt form of the compound of formula (I).

In another embodiment, the invention relates to a salt form of the compound of formula (I), wherein the salt is selected from chloride, bromide, iodide, sulfonate, triflate, and methanesulfonate.

In another embodiment, the invention relates to a compound of formula (II):

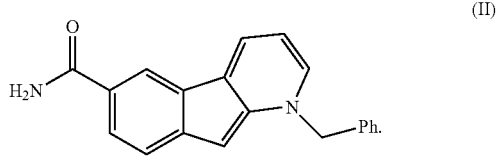 [SMILES: NC(=O)c1ccc2cc3n(Cc4ccccc4)cccc-3c2c1]

In another embodiment, the invention relates to a compound of formula (III):

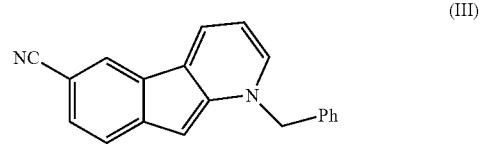 [SMILES: N#Cc1ccc2cc3n(Cc4ccccc4)cccc-3c2c1]

The invention also relates to a compound of formula (V):

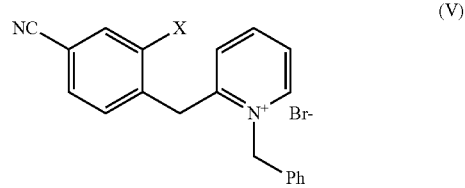

wherein X is selected from chloro, bromo and iodo.

In another embodiment, the invention relates to a compound of formula (V), wherein X is iodo.

In another embodiment, the invention relates to a compound of formula (V), wherein X is bromo.

The invention also relates to methods of making the compounds of formula (I), (II) (III) and (V).

In one embodiment, the invention relates to a method of making the compound of formula (I), comprising reacting the compound of formula (II) with hydrogen in the presence of a transition metal catalyst to provide the compound of formula (I).

In another embodiment, the invention relates to a method of making a salt form of the compound of formula (I), comprising preparing the compound of formula (I) as described in the embodiment immediately above, and contacting the compound of formula (I) with a composition comprising a salt-forming acid to provide the salt of the compound of formula (I).

In another embodiment, the invention relates to a method of making the compound of formula (II), comprising contacting the compound of formula (III) with a composition comprising hydrogen chloride and water or sulfuric acid-acetic acid mixture to provide the compound of formula (II).

In another embodiment, the invention relates to a method of making the compound of formula (III), comprising reacting a compound of formula (V)

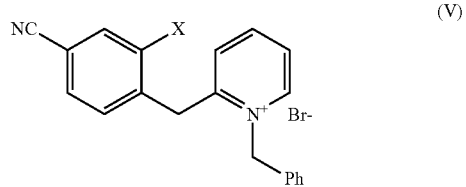

(V)

with a palladium catalyst to provide the compound of formula (III), wherein. where X is as described above.

In another embodiment, the invention relates to a method of making a compound of formula (III) as described in the embodiment immediately above, wherein X is iodo, bromo or chloro.

In another embodiment, the invention relates to a method of making a compound of formula (III) as described in any of the two embodiments immediately above, wherein the palladium catalyst is $Pd_2(dba)_3$, or $Pd(OAc)_2$.

In another embodiment, the invention relates to a method of making the compound of formula (V), comprising reacting a compound of formula (IV)

(IV)

with 2-(phenylsulfonyl)pyridine to provide the compound of formula (V), wherein X is selected from chloro, bromo and iodo.

In another embodiment, the invention relates to a method of making a compound of formula (IV) as described in the embodiment immediately above, wherein X is iodo.

In another embodiment, the invention relates to a method of making compound VI or the HCl salt form of the compound of formula (VI)

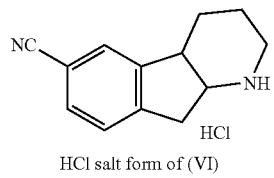

HCl salt form of (VI)

the process comprising contacting the HCl salt form of the compound of formula (I) with a dehydrating agent in organic solvent to provide the HCl salt form of the compound of formula (VI).

In another embodiment, the invention relates to a method of making the HCl salt form of the compound of formula (VI) as described in the embodiment immediately above, wherein the dehydrating agent is selected $POCl_3$, $P_2O_5$, and $SOCl_2$.

In another embodiment, the invention relates to a method of making the HCl salt form of the compound of formula (VI) as described in any of the two embodiments immediately above, wherein the agent is $POCl_3$.

In another embodiment, the invention relates to a method of making the HCl salt form of the compound of formula (VI) as described in any of the three embodiments immediately above, wherein the organic solvent is selected from dioxane, acetonitrile, toluene, 1,2-dichloroethane, and methylene chloride.

In another embodiment, the invention relates to a method of making the HCl salt form of the compound of formula (VI) as described in any of the three embodiments immediately above, wherein the organic solvent is dioxane, acetonitrile, toluene or a mixture of them.

In another embodiment, the invention relates to a method of making the compound of formula (I), the method comprising, reacting a compound of formula (IV)

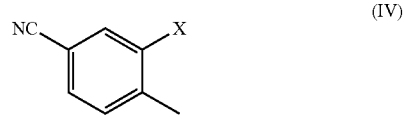

(IV)

with 2-(phenylsulfonyl)pyridine to provide the compound of formula (V),

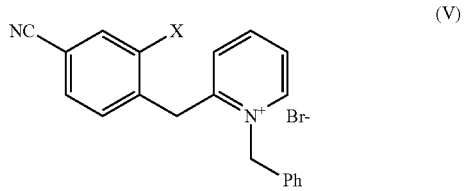

(V)

reacting the compound of formula (V) with a palladium catalyst to provide the compound of formula (III),

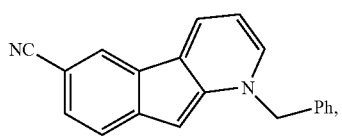

(III)

contacting the compound of formula (III) with a composition comprising hydrogen chloride and water to provide the compound of formula (II), reacting the compound of formula (II) with hydrogen in the presence of a transition metal catalyst to provide the compound of formula (I), and optionally contacting the compound of formula (I) with a composition comprising a salt-forming acid to provide the salt of the compound of formula (I).

wherein X is selected from chloro, bromo and iodo.

Further aspects of the invention are described below.

DETAILED DESCRIPTION OF THE INVENTION

Definitions
DBTA=dibenzoyl-D-tartaric
DMF=dimethylformamide
EtOAc=ethyl acetate
EtOH=ethanol
i-PrOH=isopropanol
MeOH=methanol
NaHMDS=sodium hexamethyldisilazane
Pd$_2$(dba)$_3$=tris(dibenzylideneacetone)dipalladium(0)
POCl$_3$=phosphoryl chloride
PPh$_3$=triphenylphosphine
P$_2$O$_5$=phosphorus pentoxide
SOCl$_2$=thionyl chloride
THF=tetrahydrofuran As noted above, the subject invention relates to compounds of formula (I), or salts thereof, a compound of formula (II), and methods of making the compounds.

As used herein, the term "indenopyridine derivatives" as it relates to the compounds of formulae (I)-(III) includes both compounds with fully aromatic ring systems (i.e., the compounds of formulae (II) and (III)) and a partially saturated ring system (i.e., the compound of formula (I)).

The present invention provides processes for making intermediate (4aR,9aS)-2,3,4,4a,9,9a-hexahydro-1H-indeno[2,1-b]pyridine-6-carbonitrile (A) and the 11-β-HSD1 inhibitor (4a-R,9a-S)-1-(1H-benzoimidazole-5-carbonyl)-2,3,4,4a,9,9a-hexahydro-1H-indeno[2,1-b]pyridine-6-carbonitrile (C) with fewer steps and higher yield than the processes described in WO 2011/057054. The processes of making compounds (A) and (C) described herein also advantageously avoid the use of the toxic/corrosive reagents.

The compounds of formula (I) and (II) can be prepared by the method depicted in Scheme 1 below:

Scheme 1

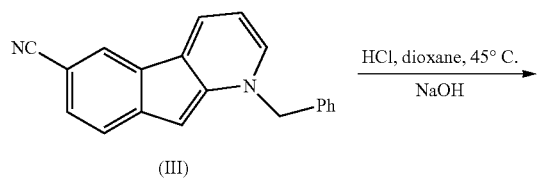

(III)

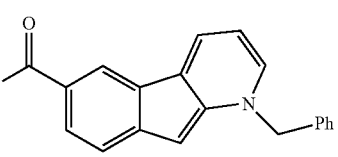

(II)

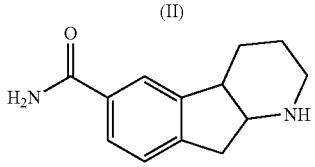

(I)

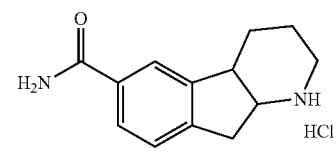

HCl salt of (I)

As depicted in Scheme 1, 4aH-indeno[2,1-b]pyridine-1-benzyl-6-carbonitrile (III) is allowed to react with a hydrogen chloride source, (e.g., aqueous HCl) followed by neutralization with base to provide 4aH-indeno[2,1-b]pyridine-1-benzyl-6-carboxamide (II). Compound (II) is then allowed to react with hydrogen in the presence of a transition metal catalyst (e.g., carbon-supported palladium) to provide the compound of formula (I) followed by treatment with a suitable salt-forming acid (e.g., hydrochloric acid) to provide the salt form of the compound of formula (I).

The compound of formula (III) can be prepared by the method depicted below in Scheme 2.

Scheme 2

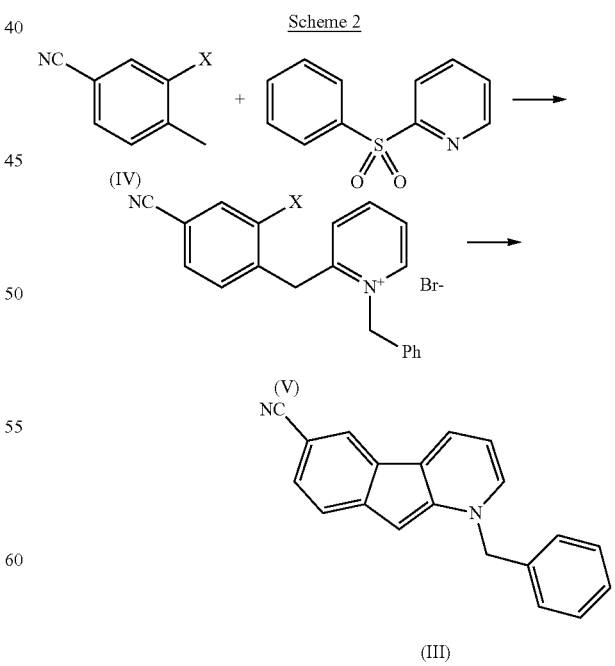

As depicted in Scheme 2, a compound of formula (IV) (where X is chloro, bromo, or iodo) is allowed to react with 2-(phenylsulfonyl)pyridine to provide the compound of formula (V). The compound of formula (V) is then allowed to react in the presence of a palladium catalyst (e.g., Pd₂(dba)₃ or Pd(OAc)₂) with or without a ligand to provide the compound of formula (III).

Salt forms of the compound of formula (I) may be prepared by reacting the compound of formula (I) (i.e., the free base form of the compound) with a sufficient amount of the appropriate salt-forming acid in water; in an organic diluent like ether, ethyl acetate, ethanol, isopropanol, or acetonitrile, or a mixture thereof; or with gaseous forms of the acid. Non-limiting examples of salt forms of the compound of formula (I) include chloride, bromide, iodide, sulfate, methanesulfonate, benzenesulfate, and mesyltate.

As further described in the Examples section (see Examples 3-5), the salt forms of the compound of formula (I) can be reacted with a dehydrating agent (e.g., phosphorus oxychloride, phosphorus pentoxide, and thionyl chloride) in organic solvent (e.g., dioxane, acetonitrile, toluene, 1,2-dichloroethane, and methylene chloride) to provide the salt form of 2,3,4,4a,9,9a-hexahydro-1H-indeno[2,1-b]pyridine-6-carbonitrile which can be resolved using chiral chromatography or by complexing with dibenzoyl-D-tartaric (D-DBTA) acid to provide (4aR,9aS)-2,3,4,4a,9,9a-hexahydro-1H-indeno[2,1-b]pyridine-6-carbonitrile (the compound of formula (C) described above and in WO 2011/057054).

In another embodiment, the invention also relates to a method of making (4aR,9aS) -2,3,4,4a,9,9a-hexahydro-1H-indeno[2,1-b]pyridine-6-carbonitrile. ½ di-benzoyl-d-tartaric acid, the method comprising contacting 2,3,4,4a,9,9a-hexahydro-1H-indeno[2,1-b]pyridine-6-carbonitrile with di-benzoyl-d-tartaric acid (D-DTBA) ("the D-DTBA contacting step") to provide (4aR,9aS)-2,3,4,4a,9,9a-hexahydro-1H-indeno[2,1-b]pyridine-6-carbonitrile·½ D-DTBA.

In another embodiment, the invention relates to the method of making 4aR,9aS)-2,3,4,4a,9,9a-hexahydro-1H-indeno[2,1-b]pyridine-6-carbonitrile·½ di-benzoyl-d-tartaric acid as described in the embodiment immediately above, wherein 2,3,4,4a,9,9a-hexahydro-1H-indeno[2,1-b]pyridine-6-carbonitrile is present in the form of a racemate.

In another embodiment, the invention relates to the method of making 4aR,9aS)-2,3,4,4a,9,9a-hexahydro-1H-indeno[2,1-b]pyridine-6-carbonitrile·½ di-benzoyl-d-tartaric acid as described in the two embodiments immediately above, wherein the molar ratio of D-DTBA to 2,3,4,4a,9,9a-hexahydro-1H-indeno[2,1-b]pyridine-6-carbonitrile in the contacting step is from about 0.1 to 2; from about 0.1 to about 1; from about 0.2 to about 0.5; or about 0.25.

In another embodiment, the invention relates to the method of making (4aR,9aS)-2,3,4,4a,9,9a-hexahydro-1H-indeno[2,1-b]pyridine-6-carbonitrile·½ di-benzoyl-d-tartaric acid as described in the two embodiments immediately above, wherein the 2,3,4,4a,9,9a-hexahydro-1H-indeno[2,1-b]pyridine-6-carbonitrile is obtained by contacting the hydrogen chloride salt of 2,3,4,4a,9,9a-hexahydro-1H-indeno[2,1-b]pyridine-6-carbonitrile with base in aqueous media to obtain 2,3,4,4a,9,9a-hexahydro-1H-indeno [2,1-b]pyridine-6-carbonitrile.

In another embodiment, the invention relates to a method of making (4a-R,9a-S)-1-(1H-benzoimidazole-5-carbonyl)-2,3,4,4a,9,9a-hexahydro-1H-indeno[2,1-b]pyridine-6-carbonitrile (C), the method comprising:

reacting a HCl salt of 2,3,4,4a,9,9a-hexahydro-1H-indeno[2,1-b]pyridine-6-carboxamide (I) salt with a dehydrating agent to provide the HCl salt of 2,3,4,4a,9,9a-hexahydro-1H-indeno[2,1-b]pyridine-6-carbonitrile:

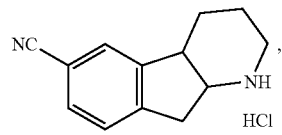

reacting the HCl salt of 2,3,4,4a,9,9a-hexahydro-1H-indeno[2,1-b]pyridine-6-carbonitrile with base followed by di-benzoyl-d-tartaric acid to provide (4aR,9aS)-2,3,4,4a,9,9a-hexahydro-1H-indeno[2,1-b]pyridine-6-carbonitrile·½ D-DTBA:

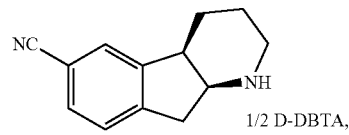 [SMILES: N#Cc1ccc2c(c1)[C@H]1CCCN[C@H]1C2]

and
reacting (4aR,9aS)-2,3,4,4a,9,9a-hexahydro-1H-indeno[2,1-b]pyridine-6-carbonitrile·½ D-DTBA with base followed by 1H-benzo[d]imidazole-5-carboxylic acid to provide the compound of formula (C).

In another embodiment, the invention relates to a method of making the HCl salt form of the compound of formula (C), the method comprising:

dissolving the compound of formula (C) as prepared according to the embodiment immediately above in an alcoholic solvent to provide a first solution; and treating the first solution treated with a second solution of HCl in an alcholic solvent to provide the HCl salt form of the compound of formula (C).

In another embodiment, the invention relates to a method of making the HCl salt form of the compound of formula (C) as described in the embodiment described immediately above, wherein the alcohol solvent is ethanol or isopropanol.

In another embodiment, the invention relates to a method of making the HCl salt form of the compound of formula (C) as described in the two embodiments described immediately above, wherein the alcohol solvent is ethanol.

In another embodiment, the invention relates to a method of making the HCl salt form of the compound of formula (C) as described in the two embodiments described above the embodiment immediately above, wherein the alcohol solvent is isopropanol.

In another embodiment, the invention relates to a method of making the compound of formula (I) as described in any of the 5 embodiments immediately above, wherein the base is aqueous NaOH and the dehydrating agent is POCl₃.

EXAMPLES

Example 1

Preparation of 4aH-indeno[2,1-b]pyridine-1-benzyl-6-carboxamide (II)

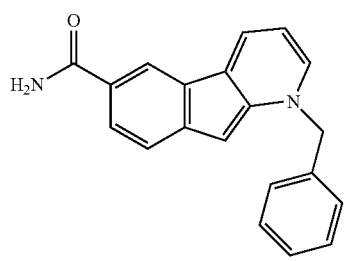
(II)

Step 1. Preparation of 2-(phenylsulfonyl)pyridine

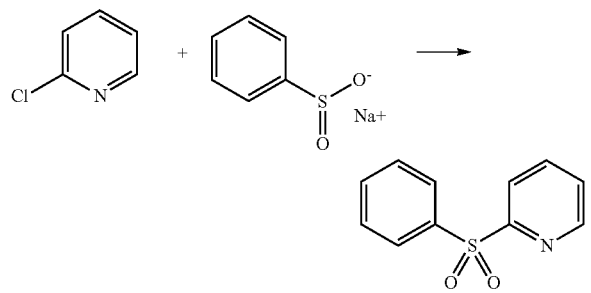

Benzensulfinic sodium salt (21.6 Kg, 131.6 mol) is charged to a reactor and treated with 60 L of a solution of acetic acid and water (3:1 vol:vol). The contents of the reactor are mixed and treated with 2-chloropyridine (30.0 Kg, 264.2 mol). The contents of the reactor are heated to 90° C. and mixed for 2 hrs. An additional solution of benzensulfinic sodium salt (26 Kg, 158.4 mol) in 60 L of acetic acid/water (3:1 vol:vol) is added to the reactor slowly over 5 hours while maintaining the contents of the reactor at 90° C. The contents of the reactor are mixed at 90° C. for about 8 hours, cooled to 20° C., and treated with water (150 L). The contents of the reactor are stirred for 30 minutes and filtered through a centrifuge filter. The filter cake is collected, treated with isopropanol (41.4 Kg, 52.4 L), and stirred at 60° C. After 30 minutes the mixture is cooled to 10° C. over 2 hours, and further mixed for 1 hour at 10° C. The mixture is filtered and the filter cake is washed with isopropanol (23.70 Kg, 30 L). The filter cake is collected and dried overnight at 50° C. to provide 2-(phenylsulfonyl) pyridine. Yield: 42.5 Kg, 194 mol; 73%.

Step 2. Preparation of 1-benzyl-2-(3-iodo-4-cyano-phenyl)methyl)pyridinium bromide

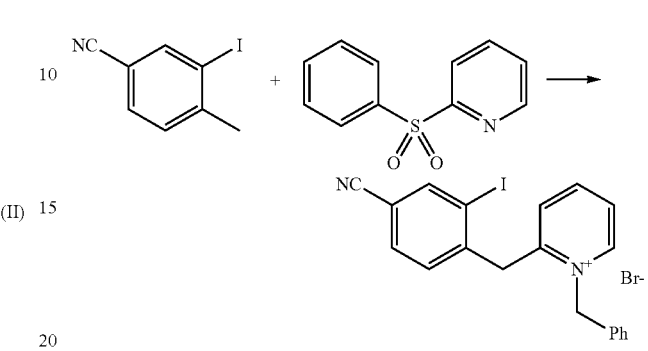

A reactor containing 3-iodo-4-methylbenzonitrile (3.49 Kg; 14.4 mol) and 2-(phenylsulfonyl)pyridine (3.0 Kg, 13.7 mol) is purged with nitrogen. The reactor is then charged with dimethylformamide (17.38 L), stirred at room temperature for 30 minutes, then cooled to 10° C. The contents of the reactor are treated drop-wise with 1 M solution of NaHMDS (sodium hexamethyldisilazane) in tetrahydrofuran (27.4 liters) over 2 hours while keeping the internal temperature below 20° C. The reaction mixture is then treated with acetic acid (783 mL) while keeping the internal temperature below 20° C. The reaction mixture is heated to 80° C. and the THF is removed by distillation. The contents of the reactor are then cooled to 25° C., treated with water (13.69 L) over 30 minutes, treated with methyl-tetrahydrofuran (MeTHF) (27.3 L), and stirred for 15 minute. The resulting organic phase is collected, washed with water (2×6.85 L), and concentrated to a minimum stirrable volume. The concentrated mixture is then treated with acetonitrile (27.4 L) and concentrated under reduced pressure to minimum stirrable volume. The acetonitrile treatment and concentration is repeated twice. The resulting concentrated mixture is then treated with dry acetonitrile (8.75 L) and benzylbromide (2.57 Kg, 15.5 mol), heated to 80° C., mixed for about 18 hours, and cooled to 25° C. The mixture is treated with MeTHF (8.75 L), stirred for about 1 hour, and filtered. The resulting filter cake is rinsed with MeTHF and dried for about 18 hours at ~50° C. to provide 1-benzyl-2-(3-iodo-4-cyano-phenyl)methyl)pyridinium bromide. Yield: 5.05 Kg, 10.28 mol; 75%.

Step 3. Preparation of 4aH-indeno[2,1-b]pyridine-1-benzyl-6-carbonitrile (III)

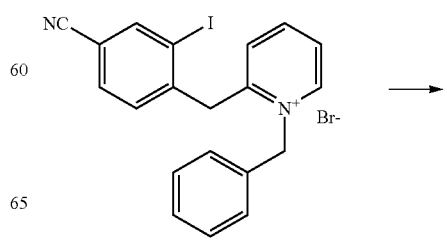

-continued

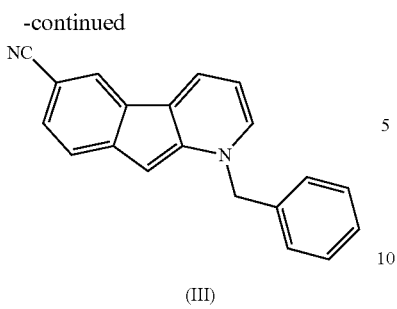

(III)

-continued

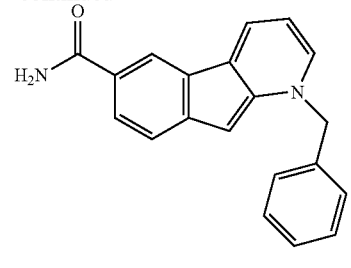

(II)

A solution of Pd₂(dba)₃ (0.64 Kg, 0.70 mol) in DMF (8.09 Kg) is prepared by charging DMF to a reactor and sparging it with nitrogen for at least 15 minutes. Pd₂ dba₃ (tris(dibenzylideneacetone)dipalladium(0)) is then charged to the reactor with stirring, and the resulting solution is sparged with nitrogen for at least 15 minutes.

A solution of triphenylphosphine (PPh₃) (0.71 Kg, 2.71 mol) in DMF (8.09 Kg) is prepared by charging DMF to a reactor and sparging it with nitrogen for at least 15 minutes. PPh₃ is then charged to the reactor with stirring, and the resulting solution is sparged with nitrogen for at least 15 minutes.

A solution of 1-benzyl-2-(3-iodo-4-cyano-phenyl)methyl)pyridinium bromide (33.72 Kg, 68.83 mol) and DMF (111.6 Kg) is treated with 1,8-diazabicyclo[5.4.0]undec-7-ene (DBU) (31.36 Kg, 206 mol). The resulting solution is sparged with nitrogen for at least 15 minutes and then treated with the entire amount of the Pd₂ dba₃ stock solution followed by the entire amount of the PPh₃ stock solution. The nitrogen sparging is maintained during the addition of the Pd₂ dba₃ and PPh₃ solutions. The contents of the reactor are then heated to 90-95° C., and the nitrogen sparging is maintained until the reaction temperature reaches 70° C. The contents of the reactor are then mixed at 90-95° C. for 12 to 18 hours, cooled to 20-25° C., and treated with water (269.76 Kg) while maintaining a reaction temperature of 40° C. The resulting mixture is stirred for at least 1 hour at 20° C. and filtered. The resulting filter cake is washed with water (2×75 L) and dried for about 18 hours at ~50° C. to provide 4aH-indeno[2,1-b]pyridine-1-benzyl-6-carbonitrile (III). Yield: 18.07 Kg, 64 mol); 93%.

Step 4. Preparation of 4aH-indeno[2,1-b]pyridine-1-benzyl-6-carboxamide (II)

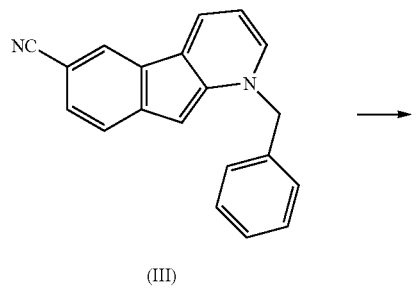

(III)

→

A stirred mixture of 4aH-indeno[2,1-b]pyridine-1-benzyl-6-carbonitrile (III) (18.78 Kg, 66.5 mol) in 1,4-dioxane (167 L) is treated with water (3.6 L) followed by HCl gas (24.2 Kg, 663 mol) at a flow rate sufficient to maintain a batch temperature of 40° C. The mixture is then heated to 45° C., stirred for 24 hours, concentrated under reduced pressure, and treated with water (36.6 L) at a rate sufficient to maintain a batch temperature of 40° C. The resulting slurry is further mixed at 40° C. until a solution forms. The contents of the reactor are then treated with a 20% NaOH solution (20 Kg) at a rate sufficient to maintain a batch temperature of 40° C. followed by treatment with water (97 Kg) over 1 hour. The resulting slurry is cooled to 20° C., stirred for 2 hours, and filtered. The resulting filter cake is rinsed with water (2×20 L) and dried for about 18 hours at 40° C. to provide 4aH-indeno[2,1-b]pyridine-1-benzyl-6-carboxamide (II). Yield: 21.05 Kg, 62.51 mol; 94%.

Example 2

Preparation of Preparation of 2,3,4,4a,9,9a-hexahydro-1H-indeno[2,1-b]pyridine-6-carboxamide (I)

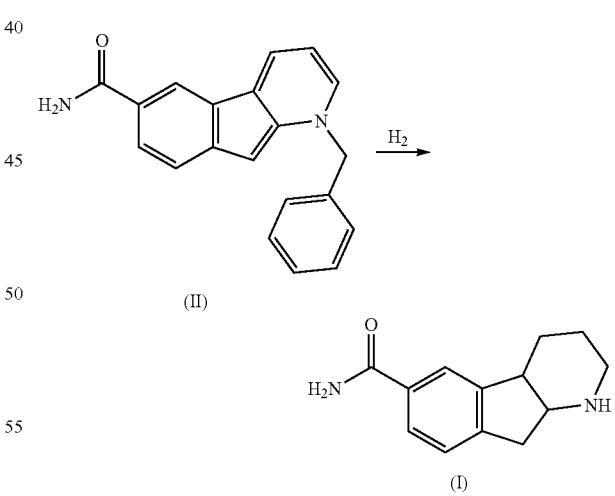

A reactor is charged with 10% Pd/C (3.52 Kg, 50% wet), Na₂CO₃ (0.707 Kg), 4aH-indeno[2,1-b]pyridine-1-benzyl-6-carboxamide (8 Kg, 26.7 mol) and MeOH (66 L). The resulting mixture is stirred and inerted 3 times with H₂. The reactor is then pressurized with H₂ to 200 PSI, the contents heated to 80° C., mixed at 80° C. for 20 hours, and cooled to 20° C. The mixture is then filtered at ambient temperature through a closed filter pre-packed with Celite-545 using N₂ pressure.

The hydrogenation reactor is rinsed with MeOH (3×18 L), and the MeOH rinses filtered through the Celilte filter. The combined MeOH filtrates contents are then concentrated under reduced pressure to about 10% of the initial volume. The resulting residue is treated with isopropanol (50 L) and concentrated under reduced pressure to about 10 L. The residue is cooled to 25° C., treated with 20 L of MeOH, and heated to 50-55° C. to provide 2,3,4,4a,9,9a-hexahydro-1H-indeno[2,1-b]pyridine-6-carboxamide (I) in free-base form.

The HCl salt form 2,3,4,4a,9,9a-hexahydro-1H-indeno[2,1-b]pyridine-6-carboxamide (I) is prepared by treating the mixture above at 50-55° C. with 6N HCl/1-PrOH (4.4 to 4.8 Kg), cooling to 20° C. over about 2 hours, stirring for about 1 hour, and filtering. The resulting filter cake is rinsed with a 1:1 (vol:vol) mixture of isopropyl acetate/MeOH (2×4 L) and dried for about 18 hours at about 50° C. to provide 2,3,4,4a,9,9a-hexahydro-1H-indeno[2,1-b]pyridine-6-carboxamide (I), hydrogen chloride salt. Yield: 5.73 Kg, 22.7 mol; 85%.

Examples 3-5 describe processes for using the compound of formula (I) as a starting material to prepare the compound of formula (C) described in WO 2011/057054.

Example 3

Preparation of 2,3,4,4a,9,9a-hexahydro-1H-indeno[2,1-b]pyridine-6-carbonitrile, hydrogen chloride salt

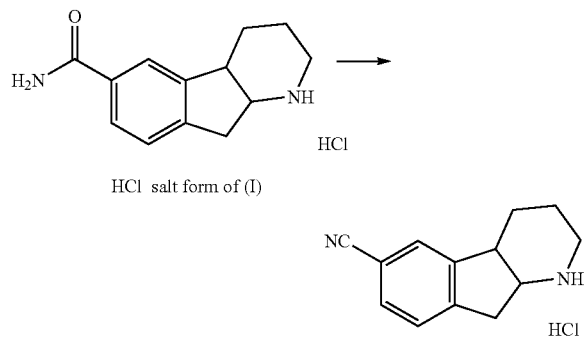

HCl salt form of (I)

A mixture of 2,3,4,4a,9,9a-hexahydro-1H-indeno[2,1-b]pyridine-6-carboxamide (I), hydrogen chloride salt (7.5 Kg, 25.2 mol) and dioxane (15 L) is stirred for 30 minutes at 25° C. and treated with POCl₃ (7.77 Kg, 50.4 mol). The mixture is heated to 80° C. over 1 hour and held at 80° C. for 2 hours. The mixture is cooled to 20-25° C., treated over about 30 minutes with a solution of water (1.376 L, 75.6 mol) in dioxane (30 L), stirred for 30 minutes, and treated with additional water (1.376 L, 75.6 mol). The resulting slurry is stirred at 25° C. for about 18 hours and filtered. The resulting filter cake is washed portion-wise with 3.0 L of 1% H₂O in 1,4-dioxane and dried for about 18 hours at ~50° C. to provide 2,3,4,4a,9,9a-hexahydro-1H-indeno[2,1-b]pyridine-6-carbonitrile (III) in the form of the hydrogen chloride salt. Yield: 4.73 Kg, 20.16 mol; 80%.

Example 4

Preparation of (4a-R,9a-S)-1-(1H-benzoimidazole-5-carbonyl)-2,3,4,4a,9,9a-hexahydro-1H-indeno [2,1-b]pyridine-6-carbonitrile (C)

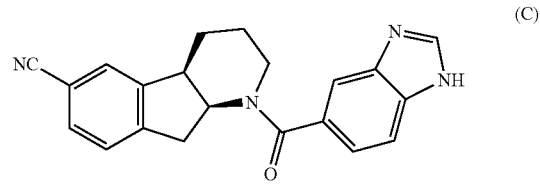 [SMILES: N#Cc1ccc2c(c1)[C@H]1CCCN(C(=O)c3ccc4[nH]cnc4c3)[C@H]1C2]

Step 1. Preparation of (4aR,9aS)-2,3,4,4a,9,9a-hexahydro-1H-indeno[2,1-b]pyridine-6-carbonitrile·½ di-benzoyl-d-tartaric acid

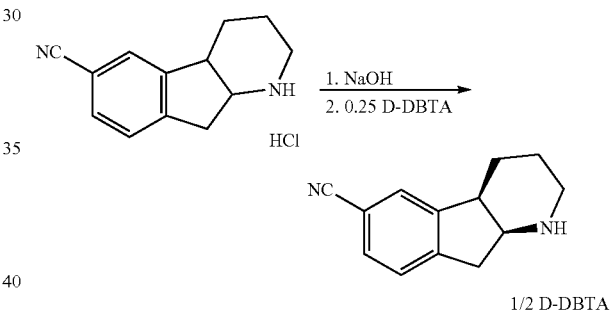

A mixture of 2,3,4,4a,9,9a-hexahydro-1H-indeno[2,1-b]pyridine-6-carbonitrile, hydrogen chloride salt (6.22 Kg, 26.5 mol), water (10 L), MeTHF (31 L) and 50% NaOH (4.4 Kg in 7 liter water) is stirred for 1 hours at 25° C. The resulting organic phase is collected, washed with 10% NaOH solution (4.25 Kg of 50% NaOH+17.2 L H₂O), and washed with 10% NaCl solution (1.42 Kg of 50% NaCl+14 L H₂O). The organic phase is concentrated, treated with acetonitrile (25 L), heated to 50° C., and treated over 4 hours with a solution of 15-18% di-benzoyl-d-tartaric acid (1.967 Kg, 5.5 mol) in acetonitrile (9.38 L). The reaction mixture is allowed to cool to 20° C. over 4 hours and filtered. The resulting filter cake is washed portion-wise with EtOH (5 L) and dried under reduced pressure. The filter cake is charged to a reactor and treated with MeOH (5.85 L) and EtOH (15.7 L). The mixture is then heated to 50° C., stirred for 2 hours, cooled to 20° C. over 2 hours and filtered. The resulting filter cake is washed portion-wise with EtOH (9 Kg) and dried for about 18 hours at 50-60° C. to provide (4aR,9aS)-2,3,4,4a,9,9a-hexahydro-1H-indeno [2,1-b]pyridine-6-carbonitrile·½ D-DTBA. Yield: 4.49 Kg, 11.93 mol: 45% (based on the amount of racemate); 90% (based on the amount of the (4aR,9aS) enantiomer in the starting racemate).

Step 2. Preparation of (4a-R,9a-S)-1-(1H-benzoimidazole-5-carbonyl)-2,3,4,4a,9,9a-hexahydro-1H-indeno[2,1-b]pyridine-6-carbonitrile

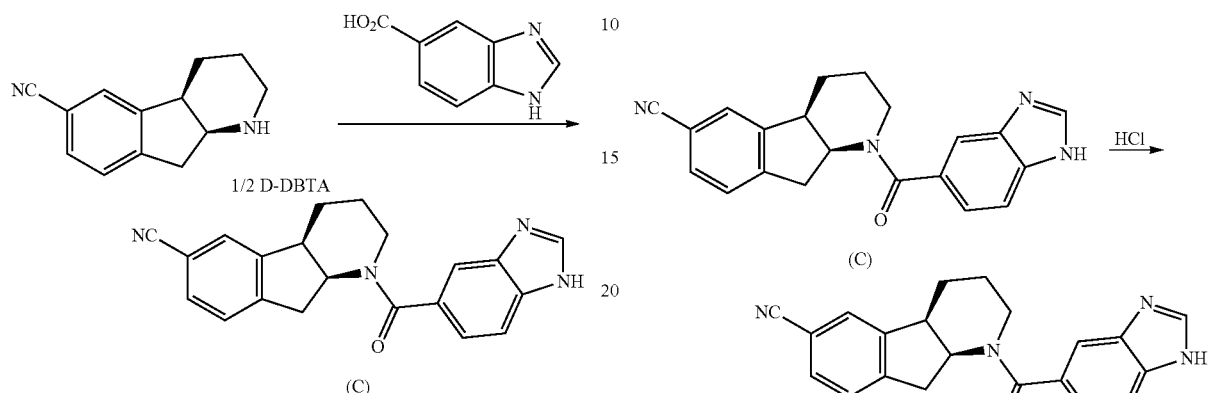

(C)

A reactor is charged with (4aR,9aS)-2,3,4,4a,9,9a-hexahydro-1H-indeno[2,1-b]pyridine-6-carbonitrile·½ D-DTBA (3.396 Kg 9 mol), dichloromethane (14.4 L) and 2N NaOH (13.5 L), and the resulting biphasic mixture is stirred for 30 minutes. The phases are allowed to separate, and the resulting organic phase is treated with 2N NaOH (4.5 L) and stirred for 10 minutes. The organic phase is collected, concentrated to about half its original volume, and treated with a solution of 1H-benzo[d]imidazole-5-carboxylic acid (1.605 Kg, 9.9 mol) in DMF (7.2 liters). The mixture is then distilled to remove any remaining dichloromethane. The mixture is then treated with 1-ethyl-3-(3-dimethyllaminopropyl)carbodiimide hydrochloride (EDC·HCl) (2.070 Kg, 10.8 mol), hydroxybenzotriazole hydrate (HOBt·H$_2$O) (1.516 Kg, 9.9 mol) and triethylamine (3.1 L). The mixture is warmed to 30° C., stirred for 2 hours, and treated with dichloromethane (12.6 L) and water (12.6 L). The resulting biphasic mixture is stirred for 30 minutes and allowed to phase separate. The organic layer is collected and the aqueous layer is washed with dichloromethane (7.2 L). The combined organic layers is charged to a reactor, treated with 2N NaOH (6.75 L) solution, and stirred for 30 minutes. The mixture is then neutralized with 6N HCl (2.07 L) to achieve a pH of 9-10. The resulting organic phase is collected, washed with water (2×10 L), concentrated to about ⅓ of its original volume, and treated with EtOAc (9 L). The resulting mixture is distilled to remove any remaining dichloromethane, cooled to 25° C., and stirred for 30 minutes. The resulting slurry is filtered, and the filter cake is washed portion-wise with EtOAc (2 L) and dried for about 18 hours at 50° C. to provide (4a-R,9a-S)-1-(1H-benzoimidazole-5-carbonyl)-2,3,4,4a,9,9a-hexahydro-1H-indeno[2,1-b]pyridine-6-carbonitrile (C) as an EtOAc solvate. Yield: 2.61 Kg (2.22 Kg after correction for purity of 85% weight % purity), 6.48 mol; 72%.

Step 3. Preparation of (4a-R,9a-S)-1-(1H-benzoimidazole-5-carbonyl)-2,3,4,4a,9,9a-hexahydro-1H-indeno[2,1-b]pyridine-6-carbonitrile (C), hydrogen chloride salt A mixture of (4a-R,9a-S)-1-(1H-benzoimidazole-5-carbonyl)-2,3,4,4a,9,9a-hexahydro-1H-indeno[2,1-b]pyridine-6-carbonitrile (C) (4.14 Kg, 12.1 mol) and 200 proof absolute EtOH (13.5 Kg) is heated to 50° C. and filtered through a pre-heated filter funnel. The warm filtrate is transferred to a pre-heated reactor and treated with 200 proof absolute EtOH (2.07 Kg). The contents of the reactor are stirred and slowly treated over 20 minutes with 0.655 Kg of a 6.34 N HCl solution in EtOH. The contents of the reactor are then seeded with 0.105 Kg of (4a-R,9a-S)-1-(1H-benzoimidazole-5-carbonyl)-2,3,4,4a,9,9a-hexahydro-1H-indeno[2,1-b]pyridine-6-carbonitrile HCl (previously made according to the procedure described below in Example 5), and stirred for 2 hours at 50° C. The contents of the reactor are treated at a constant addition rate with 0.72 Kg of a 6.34 N HCl solution in EtOH. The contents of the reactor are cooled to about 0-5° C. over 2 hours, stirred for about 4 hours, and filtered. The resulting filter cake is washed with heptane (5 Kg) and dried for 18 hours at ~50° C. to provide (4a-R,9a-S)-1-(1H-benzoimidazole-5-carbonyl)-2,3,4,4a,9,9a-hexahydro-1H-indeno[2,1-b]pyridine-6-carbonitrile (C), as the HCl salt. Yield: 4.12 Kg, 10.9 mol. An X-ray powder diffraction pattern of the product indicated it was the crystal Form II described in Example 107 of WO2012061708.

Example 5

Preparation of 4a-R,9a-S)-1-(1H-benzoimidazole-5-carbonyl)-2,3,4,4a,9,9a-hexahydro-1H-indeno[2,1-b]pyridine-6-carbonitrile HCl seed crystals The seed crystals used in Step 3 of Example 4 above are prepared according to the procedures described for crystal Form II in Example 107 of WO2012061708.

A reaction vessel is charged with (4a-R,9a-S)-1-(1H-benzoimidazole-5-carbonyl)-2,3,4,4a,9,9a-hexahydro-1H-indeno[2,1-b]pyridine-6-carbonitrile (331.5 g) and isopropanol (331.5 g), and the resulting mixture is heated at 75° C. until a homogeneous solution is formed. The solution is treated with a 5.12 M solution of HCl in isopropanol (29.7 g) followed by isopropanol (5 g) to rinse the addition vessel. The mixture is then seeded with a slurry of (4a-R,9a-S)-1-(1H-benzoimidazole-5-carbonyl)-2,3,4,4a,9,9a-hexahydro-1H-indeno[2,1-b]pyridine-6-carbonitrile hydrochloride (crystal form II) (19.88 g) in 30 g of isopropanol. (The slurry was milled for about 1 hour prior to use.) The vessel containing the seed slurry was rinsed with isopropanol (20 g) and the rinse added to the reaction vessel. The reactor contents are aged for 1 hour then treated over 4 hours with a 5.12 M solution of HCl in isopropanol (171.3 g). The mixture is cooled to 0-5° C. over 1 hour and aged at this temperature for 30 min. The resulting precipitate is collected by filtration, washed with heptane (0-5° C.), and dried under reduced pressure at 65° C. for 8 hours. Yield: 368.9 g (yield: 95%; corrected for seed charge).

Crystal form II is also obtained by the following procedure: Crystal form I (150 mg) and absolute ethanol (0.6 mL) are stirred at room temperature for one week. The precipitate is separated by filtration, washed with little absolute ethanol and dried at 40° C.

Crystal Form II can also be prepared by the following procedure: A mixture of (4a-R,9a-S)-1-(1H-benzoimidazole-5-carbonyl)-2,3,4,4a,9,9a-hexahydro-1H-indeno[2,1-b]pyridine-6-carbonitrile (26.07 g) in 200 proof absolute ethanol (104.30 g) is heated to 50° C. The resulting solution is treated with a solution of 4.587 g of a 6.55 N solution of HCl in 200 proof absolute EtOH. The mixture is then seeded with a slurry containing 0.782 g of Form II in 2.823 g EtOH. (The slurry was milled prior to use.) The reaction mixture is then aged at 50° C. for at least 2 hrs. The mixture is then treated over 2 hours with 5.045 g of a 6.55 N solution of HCl in EtOH, cooled to 0° C. over 1 hour, and aged at 0° C. for at least 1 hr. The resulting crystals are collected by filtration and dried at 70° C. under reduced pressure for at least 12 hours to provide the seed crystals.

What is claimed is:

1. A compound of formula (I):

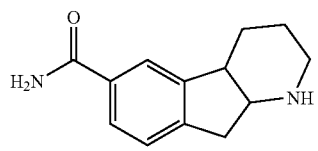

or a salt thereof.

2. The compound of formula (I) of claim 1 in free-base form.

3. The compound of formula (I) of claim 1 in the form of a salt.

4. The compound of formula (I) of claim 3, wherein the salt is selected from chloride, bromide, iodide, sulfonate, triflate, and methanesulfonate.

5. The compound of formula (I) of claim 4 in the form of a hydrogen chloride salt.

6. A method of making a compound of formula (I) of claim 1, or a salt thereof, the method comprising:

(a) reacting a compound of formula (II):

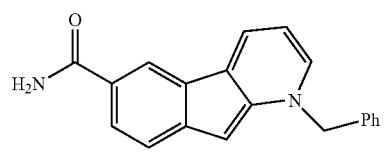

with hydrogen in the presence of a catalyst to provide the compound of formula (I), and optionally contacting the compound of formula (I) with a composition comprising a salt-forming acid to provide the salt form of the compound of formula (I).

7. The method of claim 6, wherein the compound of formula (I) is in the form of a hydrogen chloride salt, and the salt-forming acid is hydrochloric acid.

8. A method of making a compound of formula (I) of claim 1, or a salt thereof, the method comprising:

reacting a compound of formula (IV)

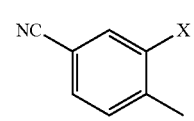

with 2-(phenylsulfonyl)pyridine to provide a compound of formula (V),

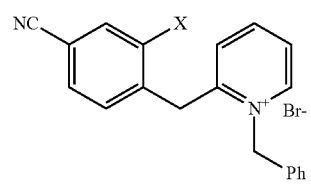

reacting the compound of formula (V) with a palladium catalyst to provide a compound of formula (III),

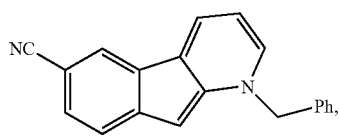

and contacting the compound of formula (III) with a composition comprising hydrogen chloride and water to provide the compound of formula (II),

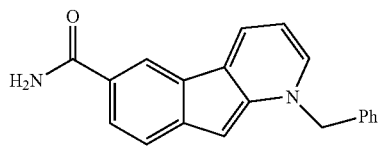 (II)

reacting the compound of formula (II) with hydrogen in the presence of a catalyst to provide the compound of formula (I), and optionally contacting the compound of formula (I) with a composition comprising a salt-forming acid to provide the salt form of the compound of formula (I)

wherein X is selected from chloro, bromo and iodo.

9. The method claim 8, wherein the compound of formula (I) is in the form of a hydrogen chloride salt, and the salt-forming acid is hydrochloric acid.

\* \* \* \* \*